United States Patent
Katsifis et al.

(10) Patent No.: US 6,379,649 B1
(45) Date of Patent: Apr. 30, 2002

(54) IMIDAZO(1,2-A)PYRIDINES AS PERIPHERAL BENZODIAZEPINE RECEPTOR BINDING AGENTS

(75) Inventors: Andrew Katsifis, Lugarno; Filomena Mattner, Ingleburn; Karin Mardon, Westlake; Vahan Papazian, Smithfield; Branko Dikic, Wollongong, all of (AU)

(73) Assignee: Australian Nuclear Science & Technology Organisation, Lucas Heights (AU)

(*) Notice: Subject to any disclaimer, the term of this patent is extended or adjusted under 35 U.S.C. 154(b) by 0 days.

(21) Appl. No.: 09/647,407

(22) PCT Filed: Apr. 6, 1999

(86) PCT No.: PCT/AU99/00254

§ 371 Date: Jan. 3, 2001

§ 102(e) Date: Jan. 3, 2001

(87) PCT Pub. No.: WO99/51594

PCT Pub. Date: Oct. 14, 1999

(30) Foreign Application Priority Data

Apr. 3, 1998 (AU) ............................................. PP 2784

(51) Int. Cl.[7] .................... C07D 471/04; A61K 31/435
(52) U.S. Cl. ....................................... 424/1.85; 546/121
(58) Field of Search .......................... 546/121; 424/1.85

(56) References Cited

U.S. PATENT DOCUMENTS

| | | | |
|---|---|---|---|
| 4,382,938 A | 5/1983 | Kaplan et al. | 544/58.4 |
| 4,460,592 A | 7/1984 | Kaplan et al. | 546/121 |
| 4,492,695 A | 1/1985 | Kaplan et al. | 546/121 |
| 4,501,745 A | 2/1985 | Kaplan et al. | 546/121 |
| 4,650,796 A | 3/1987 | George et al. | 546/121 |
| 4,767,755 A | 8/1988 | George et al. | 546/121 |
| 4,808,594 A | 2/1989 | George et al. | 546/121 |
| 4,810,711 A | 3/1989 | George et al. | 514/292 |
| 4,847,263 A | 7/1989 | George et al. | 514/300 |
| 4,891,371 A | 1/1990 | George et al. | 514/212 |
| 4,990,506 A | 2/1991 | George et al. | 514/212 |
| 5,633,237 A | 5/1997 | Hansen, Jr. et al. | 514/80 |
| 5,716,964 A | 2/1998 | Hansen, Jr. et al. | 514/300 |
| 5,721,223 A | 2/1998 | Hansen, Jr. et al. | 514/89 |

OTHER PUBLICATIONS

Almirante, L., et al., "Derivatives of Imidazole. III. Synthesis and Pharmacological activities of nitriles, amides, and carboxylic acid derivatives of imidazo[1, 2– a]pyridine." J. Med. Chem. 1969, vol. 12, 122–126.

Langer, S.Z.; Arbilla, S. "Imidazopyridines as a Tool for the Characterization of Benzodiazepine Receptors: a Proposal for a Pharmacological Classification as Omega Receptor Subtypes." Pharmacol, Biochem, Behav. 1988, 29, 763–766.

Langer, S.Z. et al., "Selectivity for Omega–Receptor Subtypes as a strategy for the Development of Anxiolytic Drugs." Pharmacopsychiatry 1990, 23, 103–107.

Jean–Jacques Burguignon; "Endogenous and Synthetic Ligands of Mitochondrial Benzodiazepine Receptors: Structure Affinity Relationships" in Peripheral Benzodiazepine Receptors, Ed. Eva Giesen–Crouse. Academic Press (Lond) 1993, Chapter 3.

Katsifis, A., et al.; "Synthesis and evaluation of [$^{123}$I] iodo–imidazo[1,2–b]pyridine as a potential tracer for the study of mitochondrial benzodiazepine receptor using SPECT." J. Lab. Com. Radiopharm. 1997, 40, 620–622.

Katsifis, A., et al., "Synthesis and Pharmacological Evaluation of an [$_{123}$I]iodoimidazo[1,2–b] Pyridazine as a Potential Tracer for the Study of the Mitochondrial Benzodiazepine Receptor Using Spect." J. Lab. Com. Radiopharm, 1997, 40, 623–625.

Trapani, G. et al., "Synthesis and Binding Affinity of 2–Phenylimidazo[1,2–a]pyridine Derivatives for both Central and Peripheral Benzodiazepine Receptors. A New Series of High Affinity and Selective Ligands for the Peripheral type." J. Med. Chem. 1997, 40, 3109–3118.

Trapani et al., "Phenylimidazo [1,2–a]pyridine Derivatives as potent and Selective Ligands for Peripheral Benzodiazepine Receptors: Synthesis, Binding Affinity, and in vivo studies." J. Med. Chem. 1999, 42, 3934–3941.

Langer et al., "Zolpidem and Alpidem: two Imidazopyridines with selectivity for $\omega_1$– and $\omega_3$– Receptor subtypes" in Biggio, G. and Costa, E. (eds.) GABA and Benzodiazapine Receptor Subtypes, Raven Press, New York, 1990, pp. 61–72.

(List continued on next page.)

Primary Examiner—Bernard Dentz
(74) Attorney, Agent, or Firm—Banner & Witcoff, Ltd.

(57) ABSTRACT

The invention provides imidazo [1,2-a] pyridines of formula (1), wherein Y is selected from F, Cl, Br, I, OH, SH, $NH_2$, CN and COOH; Z is selected from $N(R^3)C(O)R^4$ and $C(O)NR^3R^4$; $R^1$, $R^2$, $R^3$, $R^4$ can represent various radicals; m and n are independently 0, 1 or 2; and p is an integer from 1 to 4; radiolabelled derivatives and pharmaceutical compositions thereof. The compounds of the invention are useful for the diagnosis and treatment, including radiotherapy, of disorders that are characterized by an abnormal density of peripheral benzodiazepine receptors.

(1)

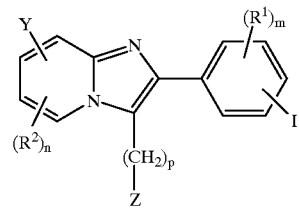

18 Claims, No Drawings

OTHER PUBLICATIONS

Allen, J., Tizot, A., "Synthesis of [$^{14}$C]zolpidem" J. Lab. Comp. Radiopharm, 1986, 23, 393–400.

Katsifis, A., Mattner, F., Mardon, K., Papazian, V., Dikic, B. "Synthesis and Evaluation of [$^{123}$I] Imidazo [1,2–a] pyridines as potential probes for the study of the peripheral benzodiazepine receptors using SPECT." 45th Annual Meeting of the Society of Nuclear Medicine, Jun. 7–11, 1998 Toronto, Canada, J. Nuc. Med., 1998, 39(5), 50D.

Mardon, K., Katsifis, A., Mattner, F., Dikic, B., Donald, A. and Chapman, J., "Synthesis and Pharmacological Evaluation of [$^{123}$I]Imidazo[1,2–a] pyridines as potential probes for the study of the peripherial benzodiazepine receptors using SPECT." 7th World Congress of Nuclear medicine, Aug. 30–Sep. 4, 1998 Berlin, Germany, Eur. J. Nuc. Med., 1998, 25(8), 890.

Cappelli A., et al., "Mapping the peripheral benzodiazepine receptor binding site by conformationally restrained derivatives of 1–(2–chlorophenyl)–N–methyl–N–(1–methylpropyl)–3–isoquinolinecarboxamide (PK11195)" J. Med. Chem. (1997), 40, 2910–2921. (Abstract only).

IMIDAZO(1,2-A)PYRIDINES AS PERIPHERAL BENZODIAZEPINE RECEPTOR BINDING AGENTS

This application is a 371 of PCT/AU99/00254 filed Apr. 6, 1999.

TECHNICAL FIELD

The present invention relates to radiolabelled imidazo[1,2-a]pyridines and related compounds which bind to peripheral benzodiazepine receptors and are useful for imaging such receptors and providing therapeutic treatment including radiotherapy.

BACKGROUND OF THE INVENTION

The peripheral benzodiazepine receptors, which are also commonly referred to as the mitochondrial benzodiazepine receptors or ω-3-receptors, are distinct from the central benzodiazepine receptors in their pharmacology, subcellular location and structural requirements. Peripheral benzodiazepine receptors are predominantly found in the peripheral organs such as kidney, heart, adrenal cortex, testis, ovaries, plasma (platelets) as well as in the glial cells and olfactory bulbs in the brain. It has also been reported that peripheral benzodiazepine receptor density is higher in tumours, such as glioma, ovarian and colon carcinoma, than in corresponding normal tissue. Recently high concentration of peripheral benzodiazepine receptors has been reported in Dunning rat prostate tumours compared to the normal ventral or dorso-lateral prostate.

The peripheral benzodiazepine receptors appear to be associated (but not exclusively) with the outer mitochondrial membrane in many tissues where they are modulated by hormones and drugs and reflect the effects of emotional stress, and hypertension. Peripheral benzodiazepine receptors in the brain have been investigated for use as markers of neurodegeneration including Huntington's disease, Alzheimer's disease, anxiety, stress, emotional disturbances, cognitive impairment, stroke, and cerebral ischemia. Several classes of ligands have been shown to exhibit high affinity binding to the peripheral benzodiazepine receptor, the most widely investigated being the benzodiazepine Ro 5-4864 (7-chloro-5-(4-chlorophenyl)-1,3-dihydro-1-methyl-2H-1,4-benzodiazepin-2-one) and the isoquinoline PK-11195 (1-(2-chlorophenyl)-N-methyl-N-(1-methylpropyl)-3-isoquinolinecarboxamide). Labelled with $^{11}C$, $^{18}F$ and $^{123}I$, these ligands have been used to map peripheral benzodiazepine receptors in the human heart and brain. Enhanced uptake of [$^{3}H$]PK-11195 has been reported in a variety of tumour cells including breast, ovarian, prostate, adrenal, brain and colon. Radiolabelling with suitable levels of radioactive iodine may be used firstly to diagnose these tumours (using radiolabels such as $^{123}I$ or $^{131}I$) and subsequently to treat them with therapeutic doses (for instance using $^{123}I$, $^{125}I$ or $^{131}I$). Furthermore, recent work has also revealed the existence of several binding domains which differ in affinity for isoquinoline and benzodiazepine ligands at different organs and species.

Various 2-aryl substituted imidazo[1,2-a]pyridines having anxiolytic, hypnotic, anticonvulsant, analgesic and other properties have been reported (Almirante L. et al., *J. Med. Chem.* 12 122–126 (1969); Langer S. Z. et al., *Pharmacol. Biochem, Behav.* 29 763–766 (1988); Langer S. Z. et al., *Pharmacopsychiatry* 23 103–107 (1990); Bourguignon, J-J., "Endogenous and Synthetic Ligands of Mitochondrial Benzodiazepine Receptors: Structure Affinity Relationships" in Giesen-Grouse. E. ed. *Peripheral Benzodiazapine Receptors*, Academic Press, London (1993)). For example $^{123}I$ labelled 6-methyl-2-(4'-iodophenyl)imidazo[1,2-a]pyridine-3-(N,N-dimethyl)acetamide has been reported as a potential tracer for the study of the peripheral benzodiazepine receptor using SPECT (Katsifis A. et al., *J. Lab. Comp. Radiopharm.* 40 620–622 (1997)).

However, the compounds which have been described previously typically exhibit strong binding to the central benzodiazepine receptors, even if they also bind to peripheral benzodiazepine receptors (see for example Anzini M. et al., *J. Med. Chem.* 39 4275–4284 (1996) and Trapani G. et al. *J. Med. Chem.* 40 3109–3118 (1997)). Hence, the prior art compounds are not sufficiently selective for peripheral benzodiazepine receptors to be useful for diagnosis or therapy of conditions associated with a high density of those receptors. Thus there is a need for substances that bind strongly to peripheral benzodiazepine receptors but do not bind strongly to central benzodiazepine receptors.

Surprisingly, the present inventors have discovered that certain 2-(iodophenyl)-imidazo[1.2-a]pyridines having an electronegative substituent especially halogen, in the pyridine nucleus exhibit strong binding to peripheral benzodiazepine receptors and much weaker binding to central benzodiazepine receptors. Hence the compounds of the present invention have superior properties, as far as the PET and SPECT imaging of peripheral benzodiazepine receptors is concerned, compared to related substances which have been reported previously.

The compounds of the present invention, appropriately labelled, are clinically useful in SPECT and PET scanning, for example to detect those cancers which express high density of the peripheral benzodiazepine receptors and/or to detect, or non-invasively diagnose, neurodegenerative disorders. The compounds of the present invention are also useful for the treatment of disorders characterised by an abnormal density of peripheral benzodiazepine receptors, such as neurodegenerative disorders and tumours.

SUMMARY OF THE INVENTION

In a first embodiment, the invention provides a compound of formula (I)

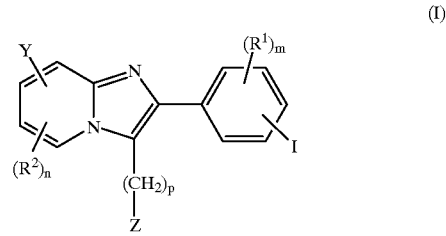

wherein
Y is selected from F, Cl, Br, I, OH, SH, $NH_2$, CN, and COOH;
Z is selected from $N(R^3)C(O)R^4$ and $C(O)NR^3R^4$;
$R^1$ and $R^2$ are independently selected from ($C_1$–$C_6$)alkyl, ($C_1$–$C_6$)alkoxy, ($C_2$–$C_6$)alkenyl, ($C_2$–$C_6$)alkynyl, ($C_3$–$C_6$)cycloalkyl, ($C_6$–$C_{12}$)aryl, ($C_6$–$C_{12}$)aryloxy, ($C_6$–$C_{12}$)aryl($C_1$–$C_6$)alkyl, heteroaryl, heteroaryl($C_1$–$C_6$)alkyl, heterocyclic, ($C_2$–$C_6$)alkanoyl and ($C_2$–$C_7$)acyl, each of which may be unsubstituted OF substituted with from 1 to 3 substituents selected from the group consisting of halogen, OH, ($C_1$–$C_4$)alkoxy, SH, NH$_2$, (C$_1$–C$_4$)alkylamino, di((C$_1$–C$_4$)alkyl)amino, carboxy, (C$_1$–C$_4$)alkoxycarbonyl. (C$_2$–C$_4$)alkanoyl, oxo, amido, CN, CNS, SCN, CNO, OCN, and NHOH;

R$^3$ and R$^4$ are each independently hydrogen or a group selected from (C$_1$–C$_4$)alkyl, (C$_2$–C$_4$)alkenyl, (C$_2$–C$_4$) alkynyl, (C$_3$–C$_6$)cycloalkyl, (C$_6$–C$_{12}$)aryl, (C$_6$–C$_{12}$) aryl(C$_1$–C$_4$)alkyl, heteroaryl, heteroaryl(C$_1$–C$_4$)alkyl, heterocyclic, (C$_1$–C$_4$)alkoxycarbonyl and (C$_2$–C$_5$)acyl, each of which may be unsubstituted or substituted with from 1 to 3 substituents selected from the group consisting of halogen, OH, (C$_1$–C$_4$)alkoxy, SH, NH$_2$, (C$_1$–C$_4$)alkylamino, di((C$_1$–C$_4$)alkyl)amino, carboxy, (C$_1$–C$_4$)alkoxycarbonyl, (C$_1$–C$_4$)alkanoyl, oxo, amido, CN, CNS, SCN, CNO, OCN, and NHOH, or R$^3$ and R$^4$ together are (C$_2$–C$_7$) alkylidene which may be optionally substituted with from 1 to 3 substituents selected from the group consisting of halogen, OH, (C$_1$–C$_4$)alkoxy, SH, NH$_2$, (C$_1$–C$_4$)alkylamino, di((C$_1$–C$_4$)alkyl)amino, carboxy, (C$_1$–C$_4$) alkoxycarbonyl, (C$_1$–C$_4$)alkanoyl, oxo, amido, CN, CNS, SCN, CNO, OCN, and NHOH;

m and n are independently 0, 1 or 2; and p is 1.

In a second embodiment, the invention provides a compound of the first embodiment which is radiolabelled.

The invention further provides a pharmaceutical composition including a compound of the first or second embodiment together with at least one pharmaceutically acceptable carrier, diluent, excipient or adjuvant.

In a third embodiment, the invention further provides a method for diagnosis of a disorder in a mammal characterised by an abnormal density of peripheral benzodiazepine receptors, the method including the steps of:

administering to the mammal an amount of a radiolabelled compound of the second embodiment sufficient to allow a detectable image of the location of the radiolabel in the body of the mammal to be recorded;

recording a image of the distribution of the radiolabel in at least part of the body of the mammal; and diagnosing the presence or absence of the disorder from the image.

In a fourth embodiment, the invention provides a method for the treatment of a disorder characterised by an abnormal density of peripheral benzodiazepine receptors in a mammal in need of said treatment, the method including administering to the mammal an effective amount of a compound of the first embodiment, or a pharmaceutical composition thereof.

In a fifth embodiment, the invention provides a method for the radiotherapy of a disorder characterised by an abnormal density of peripheral benzodiazepine receptors in a mammal in need of said radiotherapy, the method including administering to the mammal an effective amount of a compound of the second embodiment, or a pharmaceutical composition thereof.

In a sixth embodiment, the invention provides the use of a compound of the second embodiment for the manufacture of a diagnostic composition for the diagnosis of a disorder in a mammal characterised by an abnormal density of peripheral benzodiazepine receptors.

In a seventh embodiment, the invention provides the use of a compound of the first embodiment for the manufacture of a medicament for the treatment of a disorder characterised by an abnormal density of peripheral benzodiazepine receptors in a mammal in need of said treatment.

In an eighth embodiment, the invention provides the use of a compound of the second embodiment for the manufacture of a medicament for the radiotherapy of a disorder characterised by an abnormal density of peripheral benzo-diazepine receptors in a mammal in need of said radiotherapy.

In a ninth embodiment, the invention provides a compound of the second embodiment when used in a method of the third embodiment.

In a tenth embodiment, the invention provides a compound of the first embodiment when used in a method of the fourth embodiment.

In an eleventh embodiment, the invention provides a compound of the second embodiment when used in a method of the fifth embodiment.

DETAILED DESCRIPTION OF THE INVENTION

As used herein, the term "alkyl" includes within its meaning straight and branched chain alkyl groups. Examples of such groups are methyl, ethyl, propyl, isopropyl, butyl, isobutyl, sec-butyl, ter-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3dimethylbutyl, 1,2-dimethylbutyl, 1,3-dimethylbutyl, 1,2,2-trimethylpropyl and 1,1,2-trimethylpropyl.

A used herein, the term "cycloalkyl" refers to cyclic alkyl groups, or alkyl substituted cyclic alkyl groups. Examples of such groups include cyclopropyl, methylcyclopropyl, cyclobutyl, methylcyclobutyl, cyclopentyl, methylcyclopentyl, cyclohexyl and the like.

As used herein, the term "alkoxy" refers to a group of the formula alkyl-O-, wherein the alkyl group is as defined above.

As used herein, the term "alkenyl" includes within its meaning ethylenically mono- or di-unsaturated alkyl or cycloalkyl groups as previously defined. Examples of such alkenyl groups are vinyl, allyl, 1-methylvinyl, butenyl, isobutenyl, 3-methyl-2-butenyl, 1-pentenyl, cyclopentenyl, 1-methyl-cyclopentyl, 1-hexenyl, 3-hexenyl, cyclohexenyl, 1,3-butadienyl, 1,4-pentadienyl, 1,3-cyclopentadienyl, 1,3-hexadienyl, 1,4-hexadienyl, 1,3-cyclohexadienyl and 1,4-cyclohexadienyl.

As used herein, the term "alkynyl" includes within its meaning acetylenically unsaturated alkyl groups as previously defined. Examples of such alkynyl groups are ethynyl, propynyl, n-butynyl, n-pentynyl, 3-methyl-1-butynyl, n-hexynyl and methyl-pentynyl.

As used herein, the term "alkylidene" refers to optionally unsaturated divalent alkyl radicals. Examples of such radicals are —CH$_2$CH$_2$—, —CH=CH—, —CH$_2$CH$_2$CH$_2$—, —CH$_2$CH=CH—, —(CH$_2$)$_4$—, —CH$_2$CH$_2$CH=CH—, —CH$_2$CH=CHCH$_2$—, and —(CH$_2$)$_r$— where r is 5–7. The term also refers to optionally unsaturated divalent alkyl radicals in which one or more of the bonds of the radical from part of a cyclic system.

As used herein, the term "aryl" refers to single, polynuclear, conjugated and fused residues of aromatic hydrocarbons. Examples of such groups are phenyl, biphenyl, naphthyl, tetrahydronaphthyl, indenyl and azulenyl. Any available position of the aromatic residue can be used for attachment to the remainder of the molecule of formula (I).

As used herein, the term "aryloxy" refers to a group of the formula aryl-O-, wherein the aryl group is as defined above.

As used herein, the term "heteroaryl" refers to single, polynuclear, conjugated and fused residues of aromatic heterocyclic ring systems. Examples of such groups are pyridyl, 4-phenylpyridyl, 3-phenylpyridyl, thienyl, furyl, pyrryl, indolyl, pyridazinyl, pyrazolyl, pyralzinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Any available position of the heteroaromatic residue can be used for attachment to the remainder of the molecule of formula (I).

As used herein, the term "heterocyclic" refers to any 3- to 12-membered monocyclic, bicyclic or polycyclic ring containing, for 3- and 4-membered rings, one heteroatom; for 5-membered rings, one or two heteroatoms; for 6- and 7-membered rings, one to three heteroatoms; for 8- and 9-membered rings, from one to four heteroatoms; for 10- and 11-membered rings, from one to five heteroatoms; for 12-membered rings, from one to six heteroatoms; the heteroatom(s) being independently selected from oxygen, nitrogen and sulphur. The term "heterocyclic" includes any group in which a heterocyclic ring is fused to a benzene ring. Examples of heterocyclics are pyrryl, pyrimidinyl, quinolinyl, isoquinolinyl, indolyl, piperidinyl, pyridinyl, furyl, thiophenyl, tetradhyrofuryl, imidazolyl, oxazolyl, thiazolyl, pyrenyl, oxazolidinyl, isooxazolyl, isothiazolyl, isoxazolidinyl, imidazolidinyl, morpholinyl, pyrrolidinyl, pyrazolyl, pyrazolinyl, furfuryl, thienyl, benzothienyl, benoxazolyl, benzisoxazolyl, benzothiazolyl, benzoisothiazolyl, benzothiadiazolyl, tetrazolyl, triazolyl, thiadiazolyl, benzimidazolyl, pyrrolinyl, quinuclidinyl, azanorbornyl, isoquinuclidinyl and the like. Nitrogen-containing heterocyclics may be substituted at nitrogen with an oxygen atom. Sulfur-containing heterocyclics may be substituted at sulfur with one or two oxygen atoms. Configurations of heteroatoms which result in unstable heterocyclics are not included within the scope of the definition of "heterocyclic".

As used herein, the term "alkanoyl" refers to groups of the formula alkyl-C(O)O—, wherein the alkyl group is as defined above.

As used herein, the term "acyl" refers to any group of formula QC(O)—, wherein Q is amino, alkylamino, dialkylamino, alkyl, alkoxy, alkenyl, alkynyl, cycloalkyl, aryl, arylalkyl, heteroaryl, heteroarylalkyl and heterocyclic, each of which may be unsubstituted or substituted with from 1 to 3 substituents selected from the group consisting of halogen, OH, $(C_1–C_4)$alkoxy, SH, $NH_2$, $(C_1–C_4)$alkylamino, di(($C_1–C_4$)-alkyl)amino, carboxy, $(C_1–C_4)$alkoxycarbonyl, $(C_2–C_4)$alkanoyl, oxo, amido, CN, CNS, SCN, CNO, OCN, and NHOH.

A compound of the second embodiment may be radiolabelled by any convenient radionuclide. Typically, the radionuclide is an emitter of particles whose energy is suitable for imaging of the emission, or which are suitable in radiation therapy. For example, the radionuclide may be $^{11}C$, $^{18}F$, $^{76}Br$ or $^{123}I$. Usually, the radionuclide is a radionuclide of iodine, such as $^{123}I$, $^{124}I$, $^{125}I$ or $^{131}I$. For radiotherapy, the radionuclide is typically $^{123}I$, $^{125}I$ or $^{131}I$.

Compounds in accordance with the invention may be synthesised by methods which are generally known in the art. One possible synthesis of imidazo[1,2-a]pyridines in accordance with the present invention is illustrated in Scheme 1.

As shown in Scheme 1, reaction of an α-bromoacctophenone (IIb) with a 2-amino-pyridine (IIa) in ethanol or similar solvent yields an imidazo[1,2-a]pyridine (III). An aminomethyl moiety may be introduced at the 3-position by treatment of the imidazo-[1,2-a]pyridine with, for example, dimethylamine and formaldehyde in aqueous medium. The resulting aminomethyl substituent may be demethylated by known methods and acylated to yield compounds of the present invention, or it may be elaborated to an amidomethyl substituent as shown in Scheme 1. Methylation of the aminomethyl group, followed by treatment with potassium cyanide, yields the 3-cyanomethyl imidazo[1,2-a]pyridine (VI), which may be converted to a range of amidomethyl analogs (VIII) by standard methods.

Scheme 2 illustrates a method for preparing N-alkynyl and N-(iodoalkenyl) examples (IX) and (X) respectively, of compound (VIII) from carboxymethyl derivative (VII).

Scheme 1

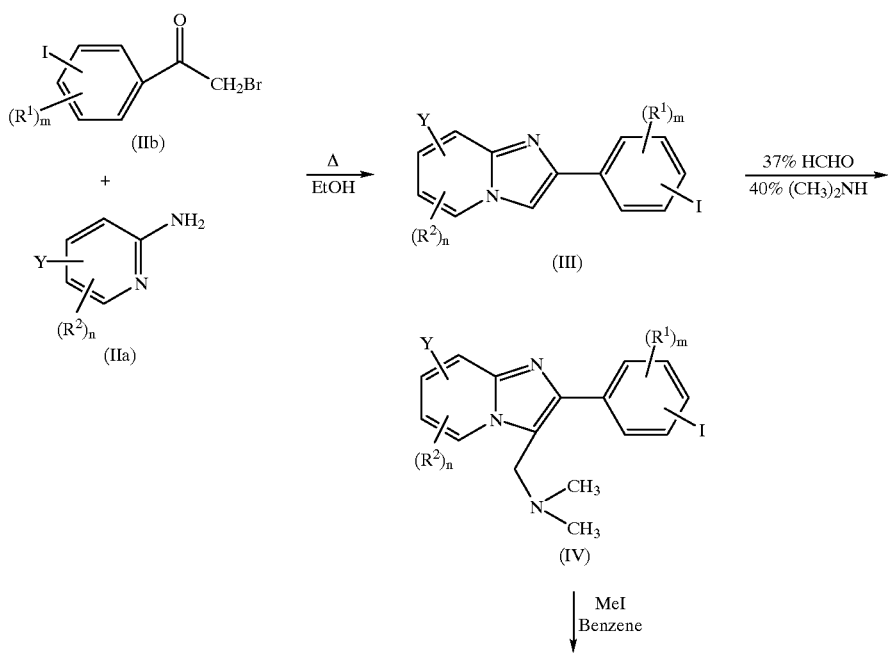

-continued

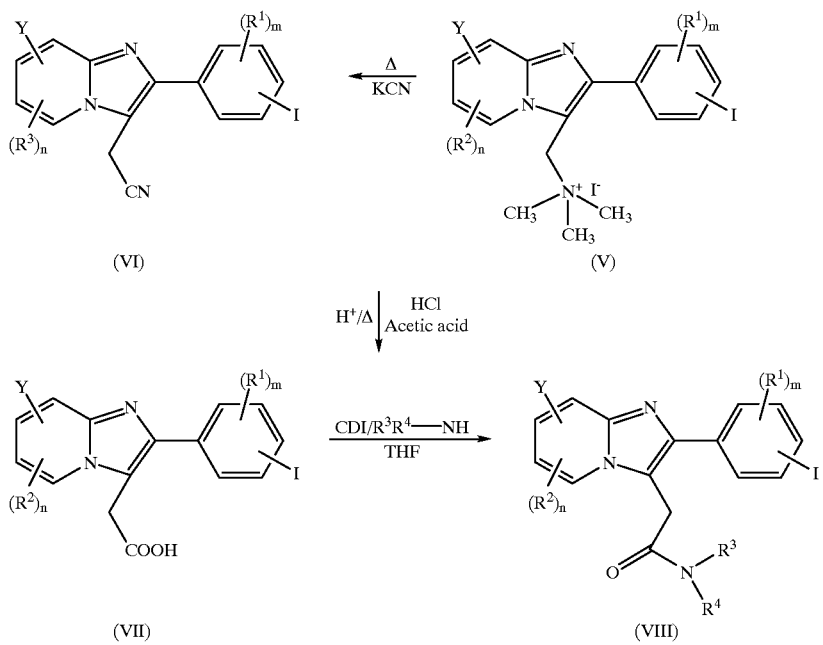

Scheme 2

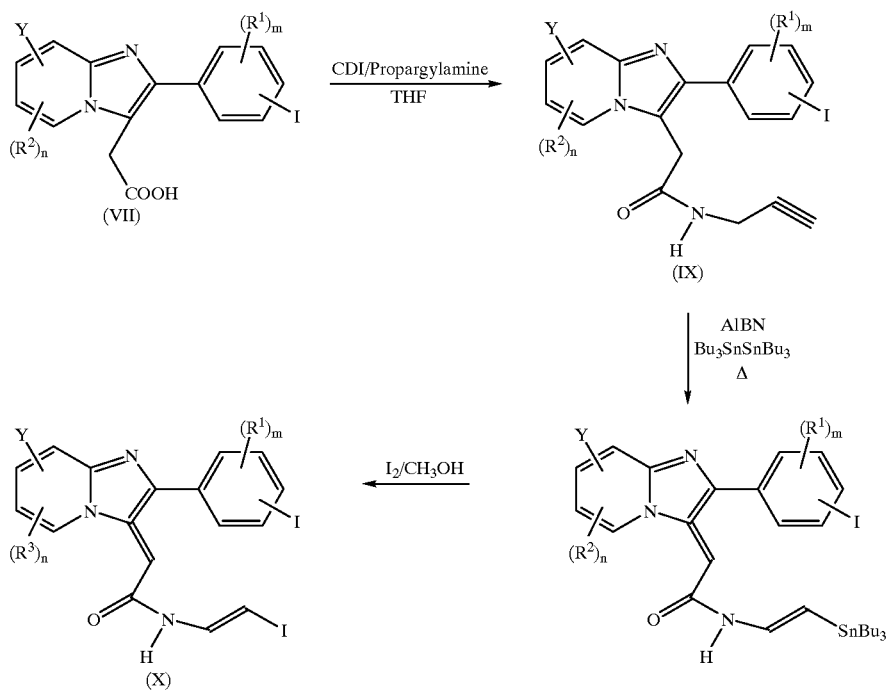

When the radionuclide in a compound of the second embodiment of the invention is a nuclide of iodine, it may conveniently be introduced as the iodo substituent on the 2-phenyl substituent of the imidazo[1,2-a]pyridine or the substituent Y in the compound of formula (I). A scheme for introducing $^{123}$I (or other isotope of iodine, *I) is illustrated in Scheme 3.

As shown in Scheme 3 starting from a 2-(bromophenyl) or 2-(iodophenyl) imidazo[1,2-a]pyridine (VII) (a 2-(bromophenyl) compound is shown) the corresponding tributyl stannane is prepared by treating the starting material with bistributyltin and palladium tetrakistriphenylphosphine in refluxing toluene, dioxane, or toluene/DMF for 6–24 hours. The resultant stannanes can be purified by column chromatography and/or by recrystallisation from ethyl acetate/hexane. The radiolabelled iodine analogs are prepared by electrophilic iododestannylation of the tributyltin derivative with Na*1 in the presence of peracetic acid, chloramine-T, iodogen or other oxidising agent in an appropriate solvent such as ethanol/methanol or acetic acid at room temperature.

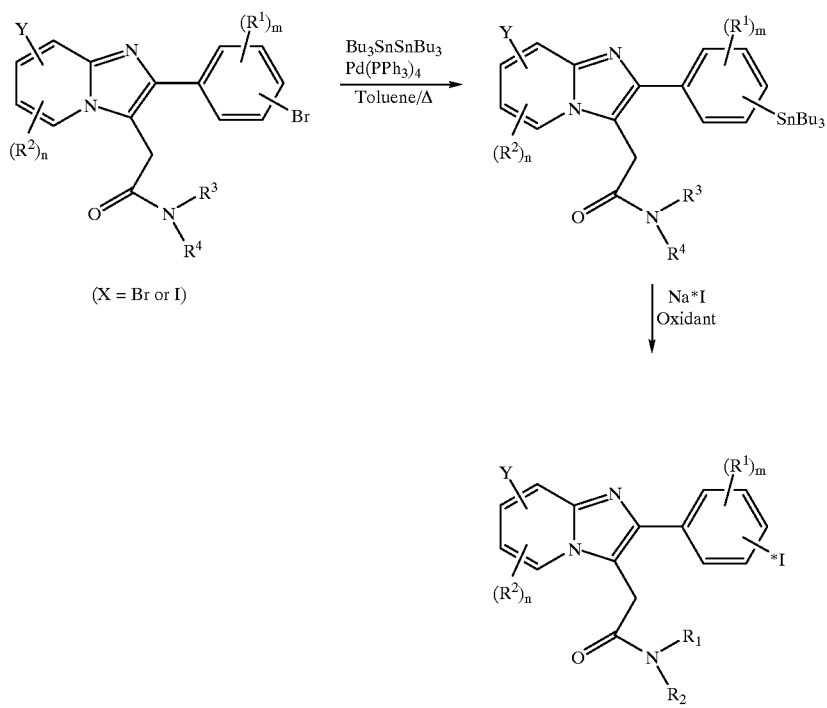

Scheme 3

Starting materials for synthesis of compounds according to the invention are either commercially available, or are known compounds, or are compounds whose synthesis presents no difficulty to a person of ordinary skill in the relevant art. In some cases, where the presence of a functional group an a substituent of a molecule may interfere with the desired synthetic step such as any of those shown in Schemes 1 to 3, it will be necessary to appropriately protect the functional group. Suitable protecting groups are generally known in the art, and are described, for example, in T. W. Greene and P. G. M. Wuts, "Protective Groups in Organic Synthesis", 2nd edition, John Wiley & Sons Inc. New York (1991), the disclosure of which is incorporated herein by reference.

A pharmaceutical composition in accordance with the invention may be administered orally, topically, parenterally, e.g. by injection and by intra-arterial infusion, rectally or by inhalation spray.

For oral administration, the pharmaceutical composition may be in the form of tablets, lozenges, pills, troches, capsules, elixirs, powders, granules, suspensions, emulsions, syrups and tinctures. Slow-release, or delayed-release, forms may also be prepared for example in the form of coated particles, multi-layer tablets or microgranules.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxyethylcellulose, methylcellulose, hydroxypropylmethylcellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as gum acacia or gum tragacanth.

For topical administration, the pharmaceutical composition may be in the form of a cream, ointment, gel, jelly, tincture, suspension or emulsion. The pharmaceutical composition may contain pharmaceutically acceptable binders, diluents, disintegrating agents, preservatives, lubricants, dispersing agents, suspending agents and/or emulsifying agents as exemplified above.

For parenteral administration, the compound of formula (I) or its salt may be prepared in sterile aqueous or oleaginous solution or suspension. Suitable non-toxic parenterally acceptable diluents or solvents include water, Ringer's solution, isotonic salt solution, 1,3-butanediol, ethanol, propylene glycol or polyethylene glycols in mixtures with water. Aqueous solutions or suspensions may further comprise one or more buffering agents. Suitable buffering agents include sodium acetate, sodium citrate, sodium borate or sodium tartrate, for example.

For rectal administration, the compound of formula (I) is suitably administered in the form of an enema or suppository. A suitable suppository may be prepared by mixing the active substance with a non-irritating excipient which is solid at ordinary temperatures but which will melt in the rectum. Suitable such materials are cocoa butter and polyethylene glycols. Suitable enemas may comprise agents as exemplified above with reference to forms for topical administration.

Suitably, an inhalation spray comprising a compound of formula (I) will be in the form of a solution, suspension or emulsion as exemplified above. The inhalation spray composition may further comprise an inhalable propellant of low toxicity. Suitable propellants included carbon dioxide or nitrous oxide.

Pharmaceutical compositions, diagnostic compositions and medicaments including comounds of the first or the second embodiment may be manufactured by methods which are generally known in the art. Typically such compositions or medicaments are prepared by grinding, crushing, blending, dispersing, dissolving, suspending, mixing, admixing, combining, emulsifying or homogenising a compound of the first or second embodiment with one or more suitable carriers, adjuvants, diluents or excipients. Combinations of two or more of the foregoing steps may also be employed.

The dosage form of the compound of formula (I) will include from 0.01% to 99% by weight of the active substance. Usually, dosage forms according to the invention will comprise from 0.1% to about 10% by weight of the active substance.

In a diagnostic method in accordance with the third embodiment of the invention, a dosage of typically from about 3 to about 25 mCi of a compound of the second embodiment is typically administered to a mammal, usually a human, in whom it is desired to diagnose the presence or absence of a disorder characterised by an abnormal density of peripheral benzodiazepine receptors. After a period of from 0.5 to 60 hours following administration of a compound of the second embodiment, more typically from 1 to 40 hours, an image of the distribution of radioactivity in the body, or part of the body, of the mammal is obtained. It will be appreciated that the lower doses are appropriate for administration to a child, and the higher dosages are more appropriate for administration for diagnosis of a tumour where imaging is to be carried out 24 hours or more after administration of the substance. The presence of a concentration of radioactivity at a site where an abnormal density of peripheral benzodiazepine receptors occurs in a mammal suffering from the disorder indicates a positive diagnosis.

A method in accordance with the fourth embodiment includes the administration to a mammal, typically a human, of a compound of the first embodiment. The administered dosage of the compound of formula (I) can vary and depends on several factors, such as the condition of the patient. Dosages will range from 0.01 mg to 200 mg per kg. Usually, the dose of the active substance will be from 0.01 mg to 10 mg per kg of body weight.

In a method in accordance with the fifth embodiment of the present invention involving the administration of a radiolabelled compound of the second embodiment, or a pharmaceutical or diagnostic composition thereof. the dosage administered is typically in the range of from 1–3 mCi per kg of body weight of the mammal, or from 10–300 mCi, more typically 50–300 mCi, per dose. The mammal is typically a human.

A therapeutic or radiotherapeutic dosage of a compound of the first or second embodiment of the invention will be determined by the attending physician in any gven circumstance, depending on factors such as the condition which is to be treated in the patient, and its severity.

Conditions for the treatment of which compounds in accordance with the invention are useful are conditions associated with abnormal density of peripheral benzodiazepine receptors such as neurodegenerative disorders, including Huntington's disease, Alzheimer's disease, anxiety, stress, emotional disturbances, cognitive impairment, stroke, and cerebral ischemia; certain tumours, such as glioma, and carcinoma of the ovary, colon, breast, prostate, brain and adrenals; neurotoxic injury, including that associated with anoxia or ischemia which may result from stroke or cardiac arrest; cognitive disorders, and in cognitive enhancement.

A compound in accordance with the invention may be administered in a single dose, or in two doses, or in multiple doses, depending on the disorder, the stage of the disorder, its response to the treatment, and any undesirable effects which may become apparent.

BEST METHOD AND OTHER METHODS FOR CARRYING OUT THE INVENTION

In one form of the present invention, the compound of formula (I) is a compound wherein:

Y is selected from F, Cl, Br, I, CN and OH;

Z is selected from $N(R^3)C(O)R^4$ and $C(O)NR^3R^4$;

$R^1$ and $R^2$ are independently selected from $(C_1-C_3)$alkyl, $(C_1-C_3)$alkoxy, $(C_2-C_3)$alkenyl, $(C_5-C_6)$cycloalkyl, phenyl, naphthyl, phenoxy, naphthyloxy, benzyl, pyridyl, furanyl, thienyl, piperidinyl, morpholinyl, tetrahydrofuranyl, dioxanyl, $(C_2-C_4)$alkanoyl and $(C_2-C_4)$acyl, each of which may be unsubstituted or substituted with from a substituent selected from the group consisting of halogen, OH, $(C_2-C_4)$alkoxy, $NH_2$, $(C_1-C_3)$alkylamino, di$((C_1-C_3)$alkyl)amino, carboxy, $(C_1-C_3)$alkoxycarbonyl, $(C_2-C_4)$alkanoyl, oxo and amido;

$R^3$ and $R^4$ are each independently hydrogen or a group selected from $(C_1-C_3)$alkyl, $(C_2-C_3)$alkenyl, $(C_5-C_6)$cycloalkyl, phenyl, naphthyl, benzyl and $(C_2-C_4)$acyl, each of which may be unsubstituted or substituted with a substituent selected from the group consisting of halogen, OH, $(C_1-C_3)$alkoxy, $NH_2$, $(C_1-C_3)$alkylamino, di$((C_1-C_3)$alkyl)-amino, carboxy, $(C_1-C_3)$alkoxycarbonyl, $(C_2-C_4)$alkanoyl, oxo and amido, or $R^3$ and $R^4$ together are $(C_2-C_3)$alkylidene which may be optionally substituted with from a substituent selected from the group consisting of halogen, OH, $(C_1-C_3)$alkoxy, $NH_2$, $(C_1-C_3)$alkylamino, di$((C_1-C_3)$alkyl)amino, carboxy, $(C_1-C_3)$alkoxycarbonyl, $(C_2-C_4)$alkanoyl, oxo and amido;

m and n are independently 0 or 1; and p is 1.

In yet another form of the present invention, the compound of formula (I) is a compound wherein n is 0.

In still another form of the present invention, the compound of formula (I) is a compound wherein p is 1, and n and m are each 0.

In even another form of the present invention, the compound of formula (I) is a compound herein p is 1, n and m are each 0, and Y is selected from F, Cl, Br, and I.

In a further form of the present invention, the compound of formula (I) is a compound wherein p is 1, n and m are each 0, and Y is selected from Cl and Br.

In a still further form of the present invention, the compound of formula (I) is a compound wherein p is 1, n and m are each 0, Y is selected from Cl and Br and Z is $C(O)NR^{13}R^{14}$, wherein $R^{13}$ and $R^{14}$ are independently selected from hydrogen, $(C_1-C_4)$alkyl and $(C_2-C_4)$alkenyl, each of which may be substituted with iodine.

In yet a further form of the invention, the compound of formula (I) is a 2-(4'-iodophenyl)-imidazo[1,2-a]pyridine-3-acetamide derivative of formula (IA)

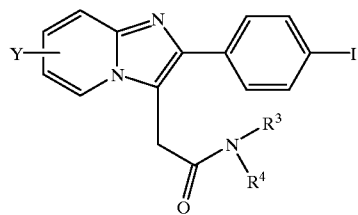

(IA)

wherein Y is halogen and $R^3$ and $R^4$ are independently selected from hydrogen, $(C_1-C_4)$alkyl and $(C_2-C_4)$alkenyl, or $R^3$ and $R^4$ taken together are $(C_2-C_3)$alkylidine.

In even a further form of the invention, the compound of formula (I) is a 2-(4'-iodophenyl)-imidazo[1,2a]pyridine-3-acetamide derivative of formula (IA), wherein Y is at the 6-position and $R^3$ and $R^4$ are independently selected from hydrogen and $(C_1-C_4)$alkyl.

In one preferred method of diagnosis of the third embodiment utilising SPECT, the compound in accordance with the invention is radiolabelled with $^{123}$I.

In another preferred method of diagnosis of the third embodiment utilising PET, the compound in accordance with the invention is radiolabelled with $^{124}$I.

In one preferred method of treatment in accordance with the fifth embodiment, the compound in accordance with the invention is radiolabelled with $^{125}$I or $^{131}$I.

EXAMPLES

Examples of specific compounds of formula (I) in accordance with the invention, and representative comparative examples, are compounds of formula (XI) as follows

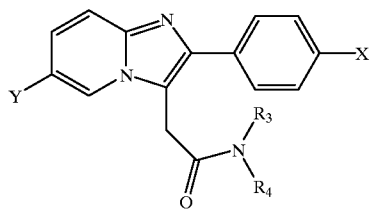

(XI)

| Example | X | Y | $R^3$ | $R^4$ | Melting Point (° C.) |
|---|---|---|---|---|---|
| 1 | I | Cl | H | $CH_3$ | 308–310 |
| 2 | I | Cl | $CH_3$ | $CH_3$ | 216–218 |
| 3 | I | Cl | $C_2H_5$ | $C_2H_5$ | 178–180 |
| 4 | I | Cl | $CH_3$ | $C_3H_7$ | 170–172 |
| 5 | I | Cl | $C_3H_7$ | $C_3H_7$ | 152–153 |
| 6 | I | Cl | $CH_3$ | $C_4H_9$ | 246–248 |
| 7 | I | Cl | $C_4H_9$ | $C_4H_9$ | 250–252 |

| Comparative Example | X | Y | $R^1$ | $R^2$ | Melting Point (° C.) |
|---|---|---|---|---|---|
| A | F | Cl | H | H | 250–252 |
| B | F | Cl | H | $CH_3$ | 254–256 |
| C | Cl | Br | H | $CH_3$ | 298–300 |
| D | Cl | Br | $CH_3$ | $CH_3$ | 234–236 |
| E | I | $CH_3$ | $CH_3$ | $CH_3$ | |

General Synthetic Procedure for Preparation of imidazo[1,2-a]pyridines in Accordance with the Invention In steps A to F described below there are provided general synthetic procedures for obtaining compounds in accordance with the invention. Identification numerals, such as (III), refer to the identification numerals used in Schemes 1 and 2 above.

A. 2-Phenyl imidazo[1,2-a]pyridines (III)

A mixture of equimolar amounts of an α-bromoacetophenone and a 2-amino-pyridine are heated to reflux in ethanol for 2 h. After cooling, the mixture is treated with 5% $NaHCO_3$ and heated to reflux for another 5 h. The mixture is then cooled to room temperature and the resultant suspension of imidazo[1,2-a]pyridine is removed by filtration. A second crop of the reaction product can be obtained after concentration or extraction of the residue with ethyl acetate. The ethyl acetate extract is washed with a little cold ethanol and water and dried ($Na_2SO_4$) and the solvent is removed by rotary evaporation.

B. 2Phenyl-3-dimethylaminomethylimidazo[1,2a]pyridines (IV)

To a mixture of the product from step A in acetic acid is added 6 equivalents of 37% aqueous formaldehyde and 1.2 equivalents of 40% aqueous dimethylamine. The mixture is stirred at 55° C. for 24 hours and then evaporated to dryness. The residual oil is cooled to ambient temperature and taken up in chloroform. The chloroform layer is washed with 2M HCl and the combined aqueous layers made alkaline to pH 12. The resultant precipitate is filtered, washed with water and dried to give a white solid.

C. 3-Dimethylaminomethyl-2-phenyl-imidazo[1,2-a]pyrdinyl methiodides (V)

A mixture of the product of step B and about 2.75 equivalents of methyl iodide in benzene is stirred for 72 hours in the dark at room temperature. The resultant white suspension is filtered, washed with ether, and dried to give the methiodide salt. This may be used directly in the next step without further purification.

D. 2-Phenyl-imidazo[1,2-a]pyridine-3-acetonitriles (VI)

The methiodide salt obtained from step C and 4 equivalents of potassium cyanide are heated to reflux in a 1:1 mixture of ethanol and water for 24 hours. A gentle stream of nitrogen is blown over the reaction mixture to remove part of the solvents and any HCN. The resulting suspension is removed by filtration to give an off white solid.

E. 2-Phenyl-imidazo[1,2-a]pyridine-3-acetic acids (VII)

A mixture of concentrated hydrochloric acid and acetic acid (1:1) is added to the nitrile obtained in step D and the mixture is heated to reflux for 15–18 hours. After the mixture is cooled to room temperature the solvents are evaporated, the residue is made a alkaline with aqueous NaOH, and the resulting solution is filtered. The filtrate is acidified with glacial acetic acid and the product is collected by filtration, washed with water and dried to give a white solid.

F. 2-Phenyl-imidazo[1,2-a]pyridine-3-acetamide (VIII)

1.2 equivalents of 1,1'-carbonyl diimidazole is added to a suspension of the acid product of step E in dry tetrahydrofuran (THF) and the resultant mixture is stirred for 1 hour at room temperature and for 1 hour at 50° C. After the mixture is cooled to room temperature it is treated with the desired amine in THF. The mixture is stirred for one hour and the solvent is evaporated. The residue is taken up in dichloromethane and washed with 10% sodium bicarbonate. The aqueous layer is then extracted three times with dichloromethane. The organic layers are combined, dried and evaporated to give the crude product. The products are purified by recrystallisation from a suitable solvent such as dichloromethane, ethyl acetate, ether, ethanol, or mixtures thereof.

G. 2-Phenyl-imidazo[1,2-a]pyridine-3-(N-(tributylstannyl)propenyl)acetamides

A mixture of the reaction product of step F, having an N-propynyl substituent on the acetamido moiety, about 1.2 equivalents of hexabutylditin and AIBN in dry toluene under nitrogen are heated to reflux for 4–5 hours. The resultant reaction mixture is then put on water and extracted with ethyl acetate. The solvent extract is dried and concentrated under vacuum. Purification of the residue by flash chromatography (ethyl acetate:petroleum spirit 40:60) yields the tri-n-butylstannane as a solid.

H. 2-Phenyl-imidazo[1,2-a]pyridine-3-(N-iodopropenyl)acetamides (X)

The stannane obtained from step G is dissolved in methanol, an equimolar amount of iodine is added and the mixture is stirred for 2 hours. The resultant reaction mixture is evaporated and dissolved in dichloromethane. The solution is washed with sodium bisulfite solution, dried and evaporated.

By the general procedure of steps A to F described above, the following compounds were prepared.

Example 1

6-chloro-2-(4'-iodophenyl)-imidazol[1,2-a]pyridine-3-(N-methyl)acetamide

Recrysallised from dichloromethane/ethanol (60–70% yield) m.p. 308–310° C. $^1$H-NMR (DMSO) δ2.64 (d, J=4.58 Hz, 3H, NCH$_3$), 4.00 (s, 2H, CH$_2$), 7.33 (dd, J=7.8 1.94 Hz, J=7.5, 1.94 Hz, H7), 7.59 (d, J=8.41 Hz, 2H, Ar), 7.64 (d, J=8.7, 9.51 Hz, H8), 7.83 (d, J=8.40 Hz, 2H, Ar), 8.21–8.23 (m, J=4.41 Hz, NH), 8.64 (d, J=1.31 Hz, H5). MS (ES) m/z: 428 (M$^{+2}$), 427 (M$^{+1}$), 426.

Example 2

6-chloro-3-(4'-iodophenyl)-imidazo[1,2-a]pyridine-3-(N,N-dimethyl)acetamide

Recrystallised from dichloromethane (60–70% yield) m.p. 216–218° C. $^1$H-NMR (DMSO) δ2.90 (s, 3H, NCH$_3$), 3.14 (s, 3H, NCH$_3$), 4.24 (s, 2H, CH2), 7.31 (dd, J=7.8 3.99 Hz, J=7.5 3.99 Hz, H7), 7.43–7.45 (m, J=8.42 Hz, 2H, Ar), 7.64 (d, J=8.7 9.61 Hz, H8), 7.83–7.85 (m, J=8.42 Hz, 2H, Ar), 8.57–8.58 (m, J=1.92, H5). MS (ES) m/z: 442.5 (M$^{+3}$), 441.5 (M$^{+2}$), 440.5 (M$^{+1}$), 439.5.

Example 3

6-chloro-2-(4'-iodophenyl)-imidazo[1,2-a]pyridine-3-(N,N-diethyl)acetamide

Recrystallised from dichloromethane/ethanol (80–90% yield) m.p. 178–180° C. $^1$H-NMR (CDCl$_3$) δ1.07 (t, J=14.27 Hz, 3H, CH$_3$), 1.14 (t, J=14.25 Hz, 3H, CH$_3$), 2.26–2.30 (m, J=7.16 Hz, 2H, NCH$_2$), 3.38–3.40 (m, J=7.07 Hz, 2H, NCH$_2$), 4.05 (s, 2H, CH$_2$), 7.17 (dd, J=7.8 1.99 Hz, J=7.5 1.93 Hz, H7), 7.39–7.41 (m, J=8.42 Hz, 2H, Ar), 7.57 (dd, J=8.7 0.71 Hz, J=8.5, 0.63 Hz, H8), 7.79–7.81 (m, J=8.43 Hz, 2H, Ar), 8.24–8.25 (m, J=2.54 Hz, H5), MS (ES) m/z: 470.5 (M$^{+3}$), 469.5 (M$^{+2}$), 468.5 (M$^{+1}$), 467.5.

Examples 4

6-chloro-2-(4'-iodophenyl)-imidazo[1,2-a]pyridine-3-(N-methyl, N-propyl)-acetamide Recrystallised from dichloromethane (50–60% yield) m.p. 170–172° C. $^1$H-NMR (CDCl$_3$) δ0.77–0.91 (m, J=51.31 Hz, 3H, CH$_3$), 1.49–1.59 (m, J=42.54 Hz, 2H, CH$_2$), 2.95 (d, J=5.28 Hz, 3H, CH$_3$), 3.14–3.49 (m, J=100.60 Hz, 3H, CH$_3$), 4.05 (d, J=12.30 Hz, 2H, CH$_2$), 7.16–7.19 (m, J=12.60 Hz, H7). 7.38–7.41 (m, J=11.01 Hz, 2H, Ar), 7.57 (d, J=8.7 9.52 Hz, H8), 7.79–7.81 (m, J=9.31 Hz, 2H, Ar), 8.23 (dd, J=28.60 Hz, H5). MS (ES) m/z; 470.5 (M$^{+3}$), 469.5 (M$^{+2}$), 468.5 (M$^{+1}$), 467.5.

Example 5

6-chloro-2-(4'-iodophenyl)-imidazo[1,2-a]pyridine-3-(N,N-dipropyl)-acetamide

Recrystallised from dichloromethane (80–90% yield) m.p. 152–153° C. $^1$H-NMR (CDCl$_3$) δ0.78 (t, J=14.77 Hz, 3H, CH$_3$) 0.87 (t, J=14.82 Hz. 3H, CH$_3$), 1.50–1.58 (m, J=33.30 Hz, 4H, 2CH$_2$), 3.12–3.16 (m, J=15.67 Hz, 2H, CH$_2$), 3.29–3.33 (m, J=15.23 Hz, 2H, CH$_2$), 4.06 (s, 2H, CH$_2$), 7.17 (dd, J=7.5 1.96 Hz, J=7.8 1.98 Hz, H7), 7.39–7.41 (m, J=8.41 Hz, 2H, Ar), 7.56 (dd, J=8.5 0.68 Hz, J=8.7 0.59 Hz, H8), 7.79–7.81 (m, J=8.41 Hz, 2H, Ar), 8.26–8.27 (m, J=2.51 Hz, H5). MS (ES) m/z: 498.5 (M$^{+3}$), 497.5 (M$^{+2}$), 496.5 (M$^{+1}$), 495.5, 288.

Example 6

6chloro-2-(4'-iodophenyl)-imidazo[1,2-a]pyridine-3-(N-methyl, N-butyl)-acetamide Recrystallised from dichloromethane (50–60% yield) m.p. 246–248° C. $^1$H-NMR (CDCl$_3$) δ0.74 (t, J=14.58 Hz, 3H, CH$_3$), 1.03–1.09 (m, J=22.53 Hz, 2H, CH$_3$), 1.20–1.27 (m, J=25.32 Hz, 2H, CH$_2$), 2.11 (s, 2H, CH$_2$), 2.26–2.31 (m, J=15.65 Hz, 2H, CH$_2$), 3.86 (s, 2H, CH$_2$), 7.13 (dd, J=7.5 1.93 Hz, J=7.8 1.95 Hz, H7), 7.54 (d, J=8.7 9.52 Hz, H8), 7.66–7.68 (m, J=8.44 Hz, 2H, Ar), 7.75–7.77 (m, J=8.41 Hz, 2H, Ar), 8.25 (d, J=1.59 Hz, H5), MS (ES) m/z 498.5 (M$^{+3}$), 497.5 (M$^{+2}$), 496.5 (M$^{+1}$), 495.5, 288.

Example 7

6-chloro-2-(4'-iodophenyl)-imidazo[1,2-a]pyridine-3-(N,N-dibutyl)-acetamide

Recrystallised from dicloromethane/ether (60–70% yield) m.p. 250–252° C. $^1$H-NMR (DMSO) δ0.84 (t, J=14.68 Hz, 6H, 2CH$_3$), 1.24–1.30 (m, J=22.39 Hz. 4H, 2CH$_2$), 1.43–1.4, (m, J=23.22 Hz, 4H, 2CH$_2$), 2.70–2.7, (m, J=15.28 Hz, 4H, 2CH$_2$), 3.77 (s, 2H, CH$_2$), 7.27 (dd, J=7.5 2.04 Hz, J=7.8 2.04 Hz, H7), 7.60 (dd, J=5.8 0.78 Hz, J=8.7 0.71 Hz, H8), 7.73–7.75 (m, J=8.50 Hz, 2H, Ar), 7.80–7.82 (rm, J=8.63 Hz, 2H, Ar), 8.65–8.66 (m, J=1.99 Hz, H5), MS (ES) m/z: 523.5 (M), 468.5, 467.5. 467.5, 413.5, 412.5, 130.

Radiolabelled Derivatives

Radiolabelled derivatives having an iodine radionuclide at the 4' position may be synthesised as generally illustrated in Scheme 3.

Conversion of tributyltin precursor to radiolabelled 4'-iodophenyl-imidazo[1,2-a]-pyridine-3-acetamide The butyltin precursor (0.1–0.5 mg) in acetic acid (200–500 μL) is treated with Na$^{123}$I (or $^{124/125/131}$I) solution followed by peracetic acid (100 μL). The peracetic acid may be prepared by the addition of hydrogen peroxide (100 μL) to acetic acid (500 μL), or commercial peracetic acid (0.3–33%) in acetic acid may be used. After 1–10 minutes, the reaction mixture is quenched with Na$_3$S$_2$O$_5$ (200 μL, 50 mg/mL) and neutralised with NaHCO$_3$ (200 μL, 50 mg/mL). The reaction mixture is injected into a semipreparative C-18 reverse phase HPLC column (Econolsil, Alltech Associates) for purification and isolation of the pure product. The mobile phase eluant is typically ethanol/water or acetonitrile/0.1M ammonium acetate at typical flow rates ranging from 2.5–4 mL/minute. The radiochemical yield of the radioiodinated products was 65–85% with the chemical and radiochemical purity exceeding 97%. The specific activity in all cases exceeded 2000 Ci/mmol. The solvent is evaporated under reduced pressure and the product residue is reconstituted in an acceptable medium suitable for intravenous injection. This medium may be sterile saline 0.9%, the product is sterile filtered through a 0.22 μ sterile filter.

In Vitro Binding Studies

In vitro binding in adrenal and kidney mitochondrial cell membranes showed that the compounds in the present invention bind to a single population of binding sites. In comparison, the in vitro binding to the central benzodiazepine receptor using rat brain homogenates was greater than 100 nM.

Methodology

In Vitro Binding Assays for Peripheral Benzodiazepine Receptors

Membrane Preparation

Male Sprague Dawley rats are sacrificed by CO$_2$ administration followed by cervical dislocation. Kidneys are removed and placed in 20 volumes of ice-cold buffer (50 nM Tris-HCl, pH 7.4) and minced finely with scissors. After homogenising the preparation with a polytron (PCU Kintematica, Bioblock, Switzerland) with one 10-second burst at a setting of 10, the suspension is centrifuged at 49,000 g for 15 minutes at 4° C. The pellets are resuspended in the previous buffer with a dounce (manual homogeniser) to yield an appropriate protein concentration. Protein measurements are made by Lowry's method using bovine serum albumin as standard.

In Vitro Binding Assay

The inhibition constant of the test compound (IC$_{50}$) is determined by incubating aliquots (0.1 mL), in triplicate, of diluted kidney membrane preparation at 4° C. for 1 hour with 7 concentrations of test compound (10$^{-6}$ to 10$^{-10}$M), together with a trace amount (2 nM) of [$^3$H]-PK11195 in a final volume of 0.5 mL. Non-specific binding is determined by blocking with cold PK11195 (10 μM). Incubation is terminated by rapid filtration through Whatman GF/B glass fiber. Each sample tube and filter is immediately washed with 3 aliquots of 5 mL ice-cold 50 nM Tris/HCl at pH 7.4. Filters are counted with a β-scintillation counter (Packard) to measure the amount of bound radioactivity. Ki and IC$_{50}$ are calculated by EBDA/Ligand, iterative non-linear least squares curve-fitting programs. (G. A. McPherson, *J. Pharmacol. Methods* 14, 213–228 (1985)).

In Vitro Binding Assays for Central Benzodiazepine Receptors

Membrane Preparation

Male Sprague Dawley rats are sacrificed by CO$_2$ administration followed by cervical dislocation. Cortex is removed and placed in 20 volumes of ice-cold buffer (50 nM Tris-HCl, pH 7.4) and minced finely with scissors. After homogenising the preparation will a polytron (PCU Kinematica, Bioblock, Switzerland) with one 10-second burst at a setting of 6, the suspension is centrifuged at 20,000 g for 20 minutes at 4° C. The pellets are resuspended in the previous buffer with a dounce (manual homogeniser). After the second centrifugation, the pellet is suspended in a final buffer (50 nM Tris/HCl, 0.32M sucrose, pH 7.4) to yield an appropriate protein concentration. Protein measurements are made by Lowry's method using bovine serum albumin as standard.

In Vitro Binding Assay

The inhibition constant of the test compound (IC$_{50}$) is determined by incubating aliquots (0.1 mL), in triplicate, of diluted cortex membrane preparation at 25° C. for 45 minutes with 7 concentrations of test compound (10$^{-6}$ to 10$^{-10}$M), together with a trace amount (2 nM) of [$^3$H]-Ro 15-1788 in a final volume of 0.5 mL. Non-specific binding is determined by blocking with cold Flumazenil (20 μM). Incubation is terminated by rapid filtration through Whatman GF/B glass fiber. Each sample tube and filter is immediately washed with 3 aliquots of 5 mL ice-cold 50 nM Tris/HCl at pH 7.4. Filters are counted with a β-scintillation counter (Packard) to measure the amount of bound radioactivity. Ki and IC$_{50}$ are calculated by EBDA/Ligand, iterative non-linear least squares curve-fitting programs (G. A. McPherson, *J. Pharmacol. Methods* 14, 213–228 (1985)).

Table 1 provides comparative in vitro binding IC$_{50}$ values for compounds of the present invention and for representative comparative compounds, including prior art compounds

TABLE 1

| Example | IC$_{50}$ (nM) PBR* | IC$_{50}$ (nM) CBR** |
|---|---|---|
| 1 | 0.99 | >1000 |
| 2 | 2.30 | 168 |
| 3 | <0.01 | >1000 |
| 4 | 0.98 | 117 |
| 5 | 3.91 | >1000 |
| 6 | 266 | >1000 |
| 7 | 177 | >1000 |
| Comparative Example | | |
| A | 3340 | 170 |
| B | >1000 | 5.9 |
| C | 33 | 15 |
| D | 90 | 56.5 |
| E | 176 | 155 |

*peripheral benzodiazepine receptor
**central benzodiazepine receptor

In Vivo Biodistribution Studies

In vivo biodistribution of radiolabelled compounds of the invention indicated high uptake in the tissues which have known PBR sites. Tables 2 to 4 show the biodistribution of the compounds of Examples 1–3, in which the iodine atom is radiolabelled, when administered to rats.

Pretreatment of the rats with known standards such as PK 11195 as well as the compound of Examples 1–7 without radiolabel (1 mg/kg) significantly reduced the uptake of activity in the tissues of interest. Pretreatment with Diazepam and Flumazenil and other central acting benzodiazepines reduced the uptake of activity of the radiolabelled compounds of the invention only marginally, indicating that the binding of the compounds of the invention in vivo is specific and selective for the peripheral benzodiazepine receptors.

TABLE 2

Biodistribution of $^{123}$-I Example 1 (% ID/g organ) in rats

| Time (Min) | Liver | Kidney | Lungs | Heart | Blood | Brain | Olfactive bulbs | Adrenals | Testes |
|---|---|---|---|---|---|---|---|---|---|
| 5 | 0.94 ± 0.12 | 1.8 ± 0.35 | 2.81 ± 0.49 | 3.25 ± 0.58 | 0.25 ± 0.04 | 0.11 ± 0.02 | 0.2 ± 0.02 | 4.51 ± 1.32 | 0.14 ± 0.03 |
| 15 | 0.7 ± 0.07 | 1.66 ± 0.13 | 1.79 ± 0.18 | 2.09 ± 0.09 | 0.16 ± 0.01 | 0.08 ± 0.01 | 0.18 ± 0.03 | 7.8 ± 2.16 | 0.22 ± 0.06 |
| 30 | 0.59 ± 0.04 | 1.25 ± 0.09 | 1.39 ± 0.14 | 1.41 ± 0.14 | 0.12 ± 0.01 | 0.06 ± 0.01 | 0.13 ± 0.02 | 11 ± 2.57 | 0.26 ± 0.05 |
| 60 | 0.47 ± 0.02 | 0.97 ± 0.07 | 0.97 ± 0.22 | 1.07 ± 0.09 | 0.1 ± 0.01 | 0.04 ± 0.001 | 0.14 ± 0.001 | 11.3 ± 0.87 | 0.28 ± 0.05 |
| 180 | 0.37 ± 0.01 | 0.61 ± 0.02 | 0.72 ± 0.05 | 0.68 ± 0.09 | 0.07 ± 0.001 | 0.03 ± 0.001 | 0.09 ± 0.02 | 9.84 ± 1.69 | 0.25 ± 0.01 |
| 240 | 0.33 ± 0.04 | 0.5 ± 0.07 | 0.63 ± 0.05 | 0.54 ± 0.05 | 0.06 ± 0.01 | 0.02 ± 0.01 | 0.07 ± 0.001 | 6.78 ± 1.27 | 0.22 ± 0.03 |
| 360 | 0.27 ± 0.01 | 0.36 ± 0.01 | 0.44 ± 0.07 | 0.38 ± 0.02 | 0.05 ± 0.001 | 0.02 ± 0.001 | 0.05 ± 0.001 | 5.7 ± 0.15 | 0.16 ± 0.03 |
| 24 Hrs | 0.09 ± 0.01 | 0.03 ± 0.001 | 0.02 ± 0.001 | 0.02 ± 0.001 | 0.01 ± 0.001 | 0 | 0.01 ± 0.001 | 0.22 ± 0.09 | 0.01 ± 0.001 |

TABLE 2

Biodistribution of $^{123}$-I Example 2 (% ID/g organ) in rats

| Time (Min) | Liver | Kidney | Lungs | Heart | Blood | Brain | Olfactive bulbs | Adrenals | Testes |
|---|---|---|---|---|---|---|---|---|---|
| 5 | 0.96 ± 0.07 | 1.62 ± 0.11 | 2.42 ± 0.26 | 2.72 ± 0.05 | 0.2 ± 0.01 | 0.16 ± 0.001 | 0.26 ± 0.04 | 0.4 ± 0.32 | 0.16 ± 0.02 |
| 15 | 1.15 ± 0.14 | 1.45 ± 002 | 1.56 ± 0.11 | 1.73 ± 0.02 | 0.14 ± 0.01 | 0.11 ± 0.01 | 0.22 ± 0.02 | 5.58 ± 0.86 | 0.25 ± 0.02 |
| 30 | 0.72 ± 0.06 | 1.03 ± 0.07 | 1.05 ± 0.16 | 1.17 ± 0.06 | 0.1 ± 0.01 | 0.7 ± 0.001 | 0.18 ± 0.001 | 7.44 ± 1.65 | 0.3 ± 0.02 |
| 60 | 0.54 ± 0.03 | 0.66 ± 0.05 | 0.74 ± 0.06 | 0.75 ± 0.07 | 0.08 ± 0.001 | 0.04 ± 0.001 | 0.13 ± 0.03 | 9.38 ± 2.04 | 0.28 ± 0.05 |
| 180 | 0.26 ± 0.05 | 0.26 ± 0.03 | 0.32 ± 0.06 | 0.26 ± 0.04 | 0.04 ± 0.001 | 0.02 ± 0.001 | 0.05 ± 0.001 | 4.8 ± 0.85 | 0.12 ± 0.02 |
| 240 | 0.22 ± 0.04 | 0.19 ± 0.03 | 0.21 ± 0.02 | 0.18 ± 0.03 | 0.04 ± 0.01 | 0.01 ± 0.001 | 0.04 ± 0.001 | 3.27 ± 0.77 | 0.6 ± 0.01 |
| 360 | 0.11 ± 0.01 | 0.09 ± 0.02 | 0.11 ± 0.03 | 0.09 ± 0.03 | 0.02 ± 0.001 | 0.01 ± 0.001 | 0.01 ± 0.001 | 1.17 ± 0.45 | 0.04 ± 0.01 |
| 24 hrs | 0.03 ± 0.01 | 0.01 ± 0.001 | 0.01 ± 0.001 | 0.01 ± 0.001 | 0 | 0 | 0 | 0.04 ± 0.001 | 0 |

TABLE 4

Biodistribution of $^{123}$-I Example 3 (% ID/g organ) in rats

| Time(Min) | Liver | Kidney | Lungs | Heart | Blood | Brain | Olfactive bulbs | Adrenals |
|---|---|---|---|---|---|---|---|---|
| 5 | 0.87 ± 0.13 | 1.73 ± 0.38 | 13.16 ± 1.24 | 2.63 ± 0.30 | 0.46 ± 0.08 | 0.33 ± 0.04 | 0.44 ± 0.08 | 2.11 ± 0.12 |
| 15 | 0.93 ± 0.06 | 2.11 ± 0.31 | 6.98 ± 1.87 | 2.39 ± 035 | 0.16 ± 0.02 | 0.2 ± 0.02 | 0.31 ± 0.03 | 2.03 ± 0.8 |
| 30 | 0.76 ± 0.01 | 2.31 ± 0.02 | 4.91 ± 0.22 | 2.44 ± 0.28 | 0.12 ± 0.03 | 0.15 ± 0.01 | 0.26 ± 0.03 | 2.42 ± 0.36 |
| 60 | 0.41 ± 0.14 | 1.87 ± 0.66 | 2.76 ± 0.80 | 2.65 ± 0.63 | 0.06 ± 0.02 | 0.08 ± 0.02 | 0.2 ± 0.07 | 2.83 ± 0.41 |
| 180 | 0.28 ± 0.02 | 1.71 ± 0.17 | 1.63 ± 0.07 | 2.59 ± 0.16 | 0.04 ± 0.001 | 0.05 ± 0.001 | 0.16 ± 0.02 | 4.1 ± 0.80 |

TABLE 4-continued

Biodistribution of $^{123}$-I Example 3 (% ID/g organ) in rats

| Time(Min) | Liver | Kidney | Lungs | Heart | Blood | Brain | Olfactive bulbs | Adrenals |
|---|---|---|---|---|---|---|---|---|
| 240 | 0.23 ± 0.03 | 1.37 ± 0.18 | 1.38 ± 0.09 | 2.49 ± 0.22 | 0.05 ± 0.001 | 0.05 ± 0.01 | 0.18 ± 0.03 | 4.32 ± 0.60 |
| 360 | 0.23 ± 0.02 | 1.43 ± 0.25 | 1.21 ± 0.27 | 2.13 ± 0.45 | 0.04 ± 0.001 | 0.05 ± 0.02 | 0.16 ± 0.04 | 5.28 ± 0.95 |
| 480 | 0.16 ± 0.01 | 0.87 ± 0.15 | 0.75 ± 0.07 | 1.48 ± 0.12 | 0.03 ± 0.001 | 0.03 ± 0.001 | 0.16 ± 0.03 | 4.22 ± 0.12 |
| 24 Hrs | 0.06 ± 0.001 | 0.25 ± 0.03 | 0.31 ± 0.06 | 0.39 ± 0.03 | 0.02 ± 0.001 | 0.01 ± 0.001 | 0.09 ± 0.001 | 4.56 ± 0.74 |
| 48 Hrs | 0.04 ± 0.001 | 0.12 ± 0.01 | 0.17 ± 0.02 | 0.17 ± 0.002 | 0.01 ± 0.001 | 0.01 ± 0.001 | 0.07 ± 0.001 | 4.87 ± 0.55 |

What is claimed is:

1. A compound of formula (I)

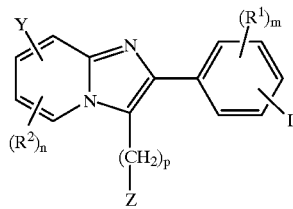

wherein

Y is selected from F, Cl, Br, I, OH, SH, $NH_2$, CN, and COOH;

Z is selected from $N(R^3)C(O)R^4$ and $C(O)NR^3R^4$;

$R^1$ and $R^2$ are independently selected from $(C_1-C_6)$alkyl, $(C_1-C_6)$alkoxy, $(C_2-C_6)$alkenyl, $(C_2-C_6)$alkynyl, $(C_3-C_6)$cycloalkyl, $(C_6-C_{12})$aryl, $(C_6-C_{12})$aryloxy, $(C_6-C_{12})$aryl$(C_1-C_6)$alkyl, heteroaryl, heteroaryl $(C_1-C_6)$alkyl, heterocyclic, $(C_2-C_6)$alkanoyl and $(C_2-C_7)$acyl, each of which may be unsubstituted or substituted with from 1 to 3 substituents selected from the group consisting of halogen, OH, $(C_1-C_4)$alkoxy, SH, $NH_2$, $(C_1-C_4)$alkylamino, di$((C_1-C_4)$alkyl)amino, carboxy, $(C_1-C_4)$alkoxycarbonyl, $(C_2-C_4)$alkanoyl, oxo, amido, CN, CNS, SCN, CNO, OCN, and NHOH;

$R^3$ and $R^4$ are each independently hydrogen or a group selected from $(C_1-C_4)$alkyl, $(C_2-C_4)$alkenyl, $(C_2-C_4)$alkynyl, $(C_3-C_6)$cycloalkyl, $(C_6-C_{12})$aryl, $(C_6-C_{12})$aryl$(C_1-C_4)$alkyl, heteroaryl, heteroaryl$(C_1-C_4)$alkyl, heterocyclic, $(C_1-C_4)$alkoxycarbonyl and $(C_2-C_5)$acyl, each of which may be unsubstituted or substituted with from 1 to 3 substituents selected from the group consisting of halogen, OH, $(C_1-C_4)$alkoxy, SH, $NH_2$, $(C_1-C_4)$alkylamino, di$((C_1-C_4)$alkyl)amino, carboxy, $(C_1-C_4)$alkoxycarbonyl, $(C_1-C_4)$alkanoyl, oxo. amido, CN, CNS, SCN, CNO, OCN, and NHOH, or $R^3$ and $R^4$ together are $(C_2-C_7)$alkylidene which may be optionally substituted with from 1 to 3 substituents selected from the group consisting of halogen, OH, $(C_1-C_4)$alkoxy, SH, $NH_2$, $(C_1-C_4)$alkylamino, di$((C_1-C_4)$alkyl)amino, carboxy, $(C_1-C_4)$alkoxycarbonyl, $(C_1-C_4)$alkanoyl, oxo, amido, CN, CNS, SCN, CNO, OCN, and NHOH;

m and n are independently 0, 1 or 2; and p is 1;

wherein at each occurrence (i) alkenyl has the meaning of ethylenically mono- or di-unsaturated alkyl or ethylenically mono- or di-unsaturated cycloalkyl;

(ii) cycloalkyl has the meaning of cyclic alkyl, or alkyl substituted cyclic alkyl;

(iii) heteroaryl has the meaning of single, polynuclear, conjugated and fused residues of aromatic heterocyclic ring systems.

2. A compound according to claim 1 wherein n is 0.

3. A compound according to claim 1 wherein:

Y is selected from F, Cl, Br, I, CN and OH;

Z is selected from $N(R^3)C(O)R^4$ and $C(O)NR^3R^4$;

$R^1$ and $R^2$ are independently selected from $(C_1-C_3)$alkyl, $(C_1-C_3)$alkoxy, $(C_2-C_3)$alkenyl, $(C_5-C_6)$cycloalkyl, phenyl, naphthyl, phenoxy, naphthyloxy, benzyl, pyridyl, furanyl, thienyl, piperidinyl, morpholinyl, tetrahydrofuranyl, dioxanyl, $(C_2-C_4)$alkanoyl and $(C_2-C_4)$acyl, each of which may be unsubstituted or substituted with from a substituent selected from the group consisting of halogen, OH, $(C_2-C_4)$alkoxy, $NH_2$, $(C_1-C_3)$alkylamino, di$((C_1-C_3)$alkyl)amino, carboxy, $(C_1-C_3)$alkoxycarbonyl, $(C_2-C_4)$alkanoyl, oxo and amido;

$R^3$ and $R^4$ are each independently hydrogen or a group selected from $(C_1-C_3)$alkyl, $(C_2-C_3)$alkenyl, $(C_5-C_6)$ cycloalkyl, phenyl, naphthyl, benzyl and $(C_2-C_4)$acyl, each of which may be unsubstituted or substituted with a substituent selected from the group consisting of halogen, OH, $(C_1-C_3)$alkoxy, $NH_2$, $(C-C_3)$ alkylamino, di$((C_1-C_3)$alkyl)amino, carboxy, $(C_1-C_3)$ alkoxycarbonyl, $(C_2-C_4)$alkanoyl, oxo and amido, or $R^3$ and $R^4$ together are $(C_2-C_3)$alkylidene which may be optionally substituted with from a substituent selected from the group consisting of halogen, OH, $(C_1-C_3)$alkoxy, $NH_2$, $(C_1-C_3)$alkylamino, di$((C_1-C_3)$ alkyl)amino, carboxy, $(CI-C_3)$alkoxycarbonyl, $(C_2-C_4)$alkanoyl, oxo and amido; and m and n are independently 0 or 1.

4. A compound according to claim 1 wherein n and m are each 0.

5. A compound according to claim 1 wherein n and m are each 0, and Y is selected from F, Cl, Br, and I.

6. A compound according to claim 5 wherein Y is selected from Cl and Br.

7. A compound according to claim 5 wherein Y is selected from Cl and Br and Z is $C(O)NR^{13}R^{14}$, wherein $R^{13}$ and $R^{14}$ are independently selected from hydrogen, $(C_1-C_4)$alkyl and $(C_2-C_4)$alkenyl, each of which may be substituted with iodine.

8. A compound of formula (I) which is a 2-(4'-iodophenyl)-imidazol[1,2-a]pyridine-3-acetamide derivative of formula (IA)

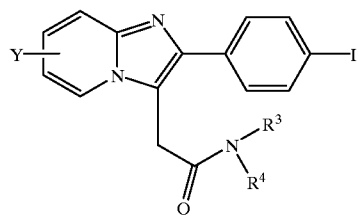

(IA)

wherein Y is halogen and $R^3$ and $R^4$ are independently selected from hydrogen, $(C_1–C_4)$alkyl and $(C_2–C_4)$alkenyl, or $R^3$ and $R^4$ taken together are $(C_2–C_3)$alkylidine.

9. A compound according to claim 8 wherein Y is at the 6-position and $R^3$ and $R^4$ are independently selected from hydrogen and $(C_1–C_4)$alkyl.

10. A compound according to any one of claims 1–9 which is radiolabelled.

11. A pharmaceutical composition including a compound according to any one of claims 1–9 together with at least one pharmaceutically acceptable carrier, diluent, excipient or adjuvant.

12. A pharmaceutical composition including a compound according to claim 10 together with at least one pharmaceutically acceptable carrier, diluent, excipient or adjuvant.

13. A method for diagnosis of a disorder in a mammal characterised by an abnormal density of peripheral benzodiazepine receptors, the method including the steps of:

administering to the mammal an amount of a radiolabelled according to claim 10 sufficient to allow a detectable image of the location of the radiolabel in the body of the mammal to be recorded;

recording a image of the distribution of the radiolabel in at least part of the body of the mammal; and diagnosing the presence or absence of the disorder from the image.

14. A method for the treatment of a disorder characterised by an abnormal density of peripheral benzodiazepine receptors in a mammal in need of said treatment, the method including administering to the mammal an effective amount of a according to any one of claims 1–9 or a pharmaceutical composition according to claim 11.

15. A method for the radiotherapy of a disorder characterised by an abnormal density of peripheral benzodiazepine receptors in a mammal in need of said radiotherapy, the method including administering to the mammal an effective amount of a compound according to claim 10, or a pharmaceutical composition according to claim 12.

16. Use of a compound according to claim 10 for the manufacture of a diagnostic composition for the diagnosis of a disorder in a mammal characterised by an abnormal density of peripheral benzodiazepine receptors.

17. Use of a compound according to any one of claims 1–9 for the manufacture of a medicament for the treatment of a disorder characterised by an abnormal density of peripheral benzodiazepine receptors in a mammal in need of said treatment.

18. Use of a compound according to claim 10 for the manufacture of a medicament for the radiotherapy of a disorder characterised by an abnormal density of peripheral benzodiazepine receptors in a mammal in need of said radiotherapy.

* * * * *